United States Patent [19]

Karydas et al.

[11] Patent Number: 5,120,364
[45] Date of Patent: Jun. 9, 1992

[54] HETEROATOM CONTAINING PERFLUOROALKYL TERMINATED NEOPENTYL SULFATES AND SALTS THEREOF

[75] Inventors: Athanasios Karydas, New York; Yung Loh, Woodside, both of N.Y.

[73] Assignee: Ciba-Geigy Corporation, Ardsley, N.Y.

[21] Appl. No.: 595,154

[22] Filed: Oct. 10, 1990

[51] Int. Cl.$^5$ .................. C09D 5/00; C09K 3/18; C07C 305/04; C07C 305/10

[52] U.S. Cl. .................. 106/287.23; 106/287.24; 106/287.25; 106/287.26; 106/287.28; 558/24; 558/25; 558/26; 558/27; 558/29; 558/30; 558/31; 558/34; 558/35

[58] Field of Search .............. 106/287.23, 287.24, 106/287.25, 287.26, 287.28; 558/24, 25, 26, 27, 29, 30, 31, 34, 35

[56] References Cited

U.S. PATENT DOCUMENTS

| | | | |
|---|---|---|---|
| 2,809,990 | 10/1957 | Brown et al. | 260/534 |
| 3,112,241 | 11/1963 | Mackenzie et al. | 162/164 |
| 3,382,097 | 5/1968 | Erby et al. | 117/141 |
| 3,409,647 | 11/1968 | Pittman et al. | 260/408 |
| 3,492,374 | 1/1970 | Le Bleu et al. | 260/950 |
| 3,901,864 | 8/1975 | Jäger | 260/89.5 |
| 3,919,361 | 11/1975 | Katsushima | 260/953 |
| 3,953,283 | 4/1976 | Wing et al. | 162/158 |
| 4,239,915 | 12/1980 | Falk | 562/481 |
| 4,302,366 | 11/1981 | Perronin et al. | 252/8.57 |
| 4,426,466 | 1/1984 | Schwartz | 523/455 |
| 4,946,992 | 8/1990 | Falk et al. | 560/227 |

FOREIGN PATENT DOCUMENTS

2024587 11/1970 Fed. Rep. of Germany .

OTHER PUBLICATIONS

Kirk-Othmer Encyclopedia of Chemical Technology, 3rd ed., vol. 16, 1991, pp. 8/2–8/3.

CA74(10): 43492g, Lalu, 1970.

Primary Examiner—Theodore Morris
Assistant Examiner—David M. Brunsman
Attorney, Agent, or Firm—Kevin T. Mansfield; Edward M. Roberts

[57] ABSTRACT

The present invention relates to perfluoroalkyl substituted sulfates and salts thereof of the formulas $$(R_f X\ CH_2)_x C(CH_2OH)_y (CH_2OSO_3-M+)_z \quad (I)$$

or $$(R_f E\ X\ CH_2)_x C(CH_2OH)_y (CH_2OSO_3-M+)_z \quad (II)$$

wherein $R_f$ is a straight or branched chain perfluoroalkyl of 1 to 18 carbon atoms or said perfluoroalkyl substituted by perfluoroalkoxy of 2 to 6 carbon atoms, E is branched or straight chain alkylene of 1 to 10 carbon atoms or said alkylene interrupted by one to three groups selected from the group consisting of —NR—, —O—, —S—, —SO$_2$—, —COO—, —OOC—, —CONR—, —NRCO—, —SO$_2$NR— and NRSO$_2$— or terminated at the $R_f$ end with —CONR— or —SO$_2$NR—, where $R_f$ is attached to the carbon or sulfur atom, and for formula II, X is —S—, —O—, —SO$_2$—, or —NR—, and for formula I, X is —CONR— or —SO$_2$NR—, where $R_f$ is attached to the carbon or sulfur atom, and where R is independently hydrogen, alkyl of 1 to 6 carbon atoms or hydroxyalkyl of 2 to 6 carbon atoms; x is 1, 2 or 3; y is 0, 1 or 2; z is 1,2 or 3; x+y+z=4; M is independently hydrogen, an alkali metal or organoammonium ion. The compounds are useful as water and oil repellants on a variety of substrates and are useful as surfactants.

10 Claims, No Drawings

HETEROATOM CONTAINING PERFLUOROALKYL TERMINATED NEOPENTYL SULFATES AND SALTS THEREOF

BACKGROUND OF THE INVENTION

This invention relates to heteroatom containing perfluoroalkyl terminated neopentyl sulfates and salts thereof and use to impart oil and water repellency to cellulosic, natural and synthetic polyamide and polyester and other compositions.

Conventional fluorochemical phosphate sizing agents are described in Kirk-Othmer Encyclopedia of Chemical Technology, 3rd. Ed. Vol. 16, pp. 812–813 (1981); and in U.S. Pat. Nos. 3,112,241; 3,492,374; 3,919,361 and 3,953,283.

Other fluorochemical sizing agents for paper are described in U.S. Pat. Nos. 2,809,990; 3,382,097; 3,409,647; 3,901,864; 4,239,915; 4,302,366 and 4,426,466.

The use of the bis-perfluoroalkyl sulfate acids according to the present invention provides thermally stable materials which are oil and water repellent at lower application levels than have been provided by previously utilized treating compositions.

DETAILED DESCRIPTION OF THE DISCLOSURE

The present invention relates to perfluoroalkyl substituted sulfates and salts thereof of the formulas

  (I)

or

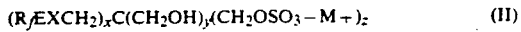  (II)

which are prepared by sulfation of perfluoroalkyl substituted alcohols of the formulas

  (III)

or

  (IV)

wherein $R_f$ is a straight or branched chain perfluoroalkyl of 1 to 18 carbon atoms or said perfluoroalkyl substituted by perfluoroalkoxy of 2 to 6 carbon atoms, or mixtures thereof, E is branched or straight chain alkylene of 1 to 10 carbon atoms or said alkylene interrupted by one to three groups selected from the group consisting of —NR—, —O—, —S—, —SO$_2$—, —COO—, —OOC—, —CONR—, —NRCO—, —SO$_2$NR— and NRSO$_2$— or terminated at the $R_f$ end with —CONR— or —SO$_2$NR—, where $R_f$ is attached to the carbon or sulfur atom, and for formula II, X is —S—, —O—, —SO$_2$—, or —NR—, and for formula I, X is —CONR— or —SO$_2$NR—, where $R_f$ is attached to the carbon or sulfur atom, and where R is independently hydrogen, alkyl of 1 to 6 carbon atoms or hydroxyalkyl of 2 to 6 carbon atoms; x is 1, 2 or 3; y is 0, 1 or 2; z is 1, 2 or 3; q is 1, 2 or 3; x+y+z=4 and x+q=4; M is independently hydrogen, an alkali metal or organoammonium ion.

It is understood that the $R_f$ group usually represents a mixture of perfluoroalkyl moieties. When the $R_f$ group is identified as having a certain number of carbon atoms, said $R_f$ group also usually concomitantly contains a small fraction of perfluoroalkyl groups with lower carbon atoms and a small fraction of perfluoroalkyl groups with higher carbon content.

Preferably the instant compounds of formula II are those where $R_f$ is perfluoroalkyl of 2 to 14 carbon atoms, or perfluoroalkyl of 2 to 6 carbon atoms substituted by perfluoroalkoxy of 2 to 6 carbon atoms, E is alkylene of 2 to 6 carbon atoms, —CONHCH$_2$CH$_2$—, —CH$_2$CH$_2$N(CH$_3$)CH$_2$CH$_2$—, CH$_2$CH$_2$SO$_2$NCH$_2$CH$_2$— or SO$_2$NCH$_2$CH$_2$—, X is —S— or —SO$_2$—, M is an organoammonium ion, x is 2 or 3, y is 0 or 1, and z is 1 or 2.

$R_f$ is preferably perfluoroalkyl of 2 to 14 carbon atoms or is perfluoroalkyl of 2 to 6 carbon atoms substituted by perfluoroalkoxy of 2 to 6 carbon atoms. More preferably, $R_f$ is perfluoroalkyl of 6–14 carbon atoms; most preferably, 6 to 12 carbon atoms.

E is preferably a branched or straight chain alkylene of 2-6 carbon atoms, or said alkylene interrupted by one group selected from the group consisting of —NR—, —O—, —S—, —SO$_2$—, —O$_2$C—, —CONR—, and —SO$_2$NR—. Most preferably E is ethylene.

Preferably X is —S—, —SO$_2$—, or —O—; most preferably —S—, or —SO$_2$—.

R is independently hydrogen, alkyl or hydroxyalkyl of up to 6 carbon atoms. Preferred alkyl groups are those containing 1–4 carbon atoms such as methyl, ethyl and the like; more preferably methyl. Preferred hydroxyalkyl groups are those containing 2–3 carbon atoms, most preferably 2-hydroxyethyl.

M is independently hydrogen, an alkali metal, ammonium or organoammonium ion. Suitable alkali metals include sodium, potassium or lithium. Preferably, sodium or potassium is the alkali metal. Suitable organoammonium ions include diethanolammonium, triethanolammonium, triethylammonium and the like, preferably triethanolammonium. Preferably M is an organoammonium ion of the formula N(R)$_4$ wherein R is as defined above.

x is preferably 2 or 3, more preferably 2.

y is preferably 0 or 1, more preferably 1.

z is preferably 1 or 2, more preferably 1.

The novel sulfate derivatives can be obtained directly from heteroatom containing $R_f$-terminated neopentyl glycols of the general formulas (III) and (IV). The neopentyl alcohols can be sulfated by reaction with sulfuric acid, chlorosulfonic acid, fuming sulfuric acid, sulfamic acid or SO$_2$/Freon 113. The reaction can be carried out in an inert solvent or without solvent. Preferred reaction temperatures are low, usually 10°-50° C. Neutralization of the sulfate, usually to pH 7-10 is accomplished by the addition of amines. As the reaction tends to be exothermic, cooling of the vessel may be advantageously employed. The neutralization is preferably conducted between 0° and about 40° C. Where the inert diluent is organic in nature, diethylene glycol dimethyl ether or the like, the ammonium or amine salts reaction product can be recovered by precipitation, or evaporation of the diluent. The ammonium or amine salt need not be separated from the solvent media. The amines should be water soluble mono- or polyamines having a water solubility of at least 2% by weight. Suitable amines are aminomethane, aminoethane, 1-aminopropane, 2-aminopropane, 1-aminobutane, -amino-2-methyl-propane, 1,1-dimethylethylamine, 1-aminopentane, isoamylamine, tert-amylamine, allylamine, dimethylamine, diethylamine, diisopropylamine, trimethylamine, triethylamine, tri-n-butylamine, ethylenediamine, 1,2-propanediamine, trimethylenediamine, 1,3-diaminobutane, 1,4-diaminobutane, hexamethylene diamine, diethylenetriamine, triethylenetriamine, tetraethylenepentamine, polyethyleneimine having an average of about 20, 80, 120 or 200 units, diethylaminopropylamine, ethanolamine, diethanolamine, triethanolamine, ethylenediamine tetraacetic acid, nitrilotrisacetic acid, N-(hydroxyethyl)-ethylenediamine, N,N''-bis(hydroxyethyl)-diethylenetriamine, N,N,N',N'-tetrakis-(2-hydroxypropyl)-ethylenediamine N-(2-hydroxypropyl)-ethylene-diamine, cyclohexylamine, dicyclohexylamine, and

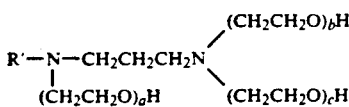

where R' is tallow fatty alkyl and $a+b+c$ is 3, 10 or 15, fatty diethanolamines, mono-, di-, and tri-isopropanolamines and polyoxyethyleneamines.

Quaternary ammonium salts can also be obtained from tetraalkylammonium bases by neutralization.

Alternately, alkali metal hydroxides such as lithium hydroxide, sodium hydroxide and potassium hydroxide may be used for neutralization.

The perfluoroalkyl sulfates of the present invention can be used containing 5 to 80% by weight of the neutralized sulfate salt, optionally in situ by the addition as the unneutralized sulfate to a basic aqueous application formulation. Alternately it is prepared as a concentrate in the presence of excess base. The perfluorochemical is applied from water or from a solvent soluble in water to at least 0.1%.

For topical application, suitable aqueous dilutions contain, advantageously, about 0.01% to about 5%, preferably 0.02% to about 2%, by weight of the perfluoroalkyl salts at use dilution. Conventional adjuvants such as water repellant assistants, bacteriostats, coloring agents, surface conditioners and the like, may be included, e.g. in an amount of between about 0.01% and about 10% By weight in the emulsion. Also, sizing agents, where the emulsion is to be used on cellulosic substrates, may be present in the amounts of from about 0.01% to about 10% by weight.

The sizing agent may be a natural sizing agent such as animal glue, asphalt emulsions, wax emulsions, rosins, starches; a semisynthetic sizing agent such as a fatty acid salt or complex, a fortified rosin, e.g., trisodium maleoprimaric acid salt, sodium alginate or sodium carboxymethylcellulose; or a synthetic sizing agent such as an alkylketene dimer, alkylsuccinic anhydrides, polyvinyl alcohol, styrene-maleic anhydride polymers, and the like. Also mixtures thereof may be used.

Additionally, an emulsifier can be optionally present in an amount of between about 0.001% to about 3% by weight.

Thus, suitable dilutions for topical application contain;
(a) about 0.01 to about 5% by weight of the perfluoroalkyl sulfates of the instant invention;
(b) 0 to about 3% by weight emulsifier;
(c) 0 to about 5% water repellant assistant, filler, bacteriostat, coloring agent or surface conditioner adjuvant, or mixtures thereof;
(d) 0 to about 10% sizing agent; and
(e) the remainder water.

These formulations are applied to the surface of the cellulosic or natural or synthetic polyamide material by conventional techniques, including padding, spraying, coating, washing, and brushing. After application, the treated surface is dried, with or without an intermediate washing stage. The resulting surface is thus rendered water and oil resistant.

For use as a sizing agent to obtain oil and water repellency, the dilution of the instant aqueous formulations advantageously contain from about 0.0005 to about 0.2% by weight of the perfluoroalkyl sulfates. The formulations for dilution may be prepared as a concentrate containing between about 5% and about 80% by weight, preferably about 30 to about 80% by weight, of the salt.

Suitable cellulosic and natural substrates for topical application include paper, non-woven fabrics, textiles, paperboard, wood, wood fiber products such as plywood, hair, including wool, hides, leather, and feathers. Synthetic substrates include nylon fibers and textiles.

While the instant formulations are suitable for rendering a variety of materials oil and water repellant, they are particularly advantageous in rendering articles made from paper pulp, such as paper trays, paper plates and analogous paper articles, both oleophobic and hydrophobic.

In order to further increase the efficiency of application it is conventional to treat the paper pulp with a cationic agent, or retention aid such as a cationically modified starch, which is adsorbed by the paper pulp and, consequently, tends to increase the amount of fluorochemical transferred to the cellulose substrate.

Suitable cationic agents, conventionally used to treat cellulose materials such as paper pulp, include conventional cationic modified starches, such as LOK-SIZE 30, INTER-BOND C, from A. E. Staley; CATO 2, CATO 15 and CATO 17 from Nat. Starch, cationic modified aminoplast resins such as KYMENE 557H from Hercules Inc.; cationic polymers such as HYPO WB-4000 with W. R. Grace Inc.

Suitable cationic resins are described in Bates, "Polyamide-Epichlorhydrin Wet Strength Resin TAPPI, 52, (6) 1969 and in U.S. Pat. Nos. 3,655,506 and 4,299,654.

Jointly with the perfluoroalkyl sulfates of the product invention, can be added one or more of wide choice of water proofing sizing agents selected from classes such as alkyl anhydrides, e.g. FIBRON 68; from Nat. Starch; alkyl ketene dimers e.g. AQUAPEL 360 XC or HERCON 40; from Hercules, Inc., polyurethane emulsions, e.g. acrylic resins, e.g. stearyl amine surfactants, e.g. ETHOMEEN 18/25 from Akzo Chemie complexed with a fatty acid, e.g. stearic acid; NEOFAT 14, NEOFAT 47 or HYSTRENE 9718 from Akzo Chemie. Suitable hydrophobic sizing agents are described by Davis, et al., TAPPI, 39 (1) pp 21-23 (1956) and in U.S. Pat. Nos. 4,243,481 and 4,279,794.

The amount of adjuvant and sizing agent used for treating paper is of the range specified for topical application, supra.

Thus, for internal or external sizing of paper pulp suitable aqueous dilutions contain:
(a) about 0.0005 to 0.1% by weight of the perfluoroalkyl sulfates of the present invention;
(b) 0 to about 0.05% by weight emulsifier;

(c) 0 to about 5% by weight filler, bacteriostat, fungicide, coloring agent or surface conditioner adjuvant, or retention aid;
(d) 0 to about 10% sizing agent; and
(e) the remainder water.

The following examples are intended for illustrative purposes only, and are not intended to restrict the scope of the invention in any way. All parts are by weight unless otherwise specified.

SAMPLE PREPARATION AND TESTING

Pad Application of Fluorochemicals on an External Size

Samples of fluorochemicals are diluted to the test application levels with distilled water. The solutions are added to a 4% aqueous solution of paper maker's starch and applied to unsized paper by padding (paper dipped through starch solution, then passed through single nip rollers). The resulting sheets are dried at ambient conditions for 15 minutes, then 3 minutes at 200° F. in an "Emerson Speed Drier" (heated metal plate with canvas cover).

Grease Resistance Test

Creased test papers are placed over a grid sheet imprinted with 100 squares. 5 grams of sand is placed in the center of the crease. A mixture of synthetic oil and dye for visualization is pipetted onto the sand and the samples are maintained at 60° C. for 24 hours.

Evaluation is determined by the percentage of the grid which is stained.

| Kit No. | Volume Castor Oil | Volume Toluene | Volume Heptane |
|---|---|---|---|
| 1 | 200 | 0 | 0 |
| 2 | 180 | 10 | 10 |
| 3 | 160 | 20 | 20 |
| 4 | 140 | 30 | 30 |
| 5 | 120 | 40 | 40 |
| 6 | 100 | 50 | 50 |
| 7 | 80 | 60 | 60 |
| 8 | 60 | 70 | 70 |
| 9 | 40 | 80 | 80 |
| 10 | 20 | 90 | 90 |
| 11 | 0 | 100 | 100 |
| 12 | 0 | 90 | 110 |

The "kit value" is defined as the highest number solution that will stand on the surface of the plate for 15 seconds in the form of drops without failing. Failure is detected by pronounced darkening caused by penetration. The darkening of even a small fraction of the area under drop is considered failure.

EXAMPLE 1

2,2-Bis(1,1,2,2-tetrahydroperfluorodecylthiomethyl)-1,3-propanediol (20.0 g, 0.019 mole) is charged into a three-neck flask with diethylene glycol dimethyl ether (22.5 g). Stirring is started under nitrogen flow. The solution is cooled to 0° C. and 95% H₂SO₄ (7.5 g, 0.076 mole) is added dropwise to the solution so the temperature does not exceed 25° C. The addition is complete in ten minutes. The solution is allowed to warm to 25° C. and stirring is continued for 120 hours. Triethanol amine (20.9 g, 0.14 mole) in H₂O (64.8 g) is slowly added to the solution so the temperature does not exceed 45° C. The pH is 7.77 and the solution contains 18.2% actives.

A negative FAB mass spectrum in a glycerol matrix reveals the monosulfate (I) as the major component.

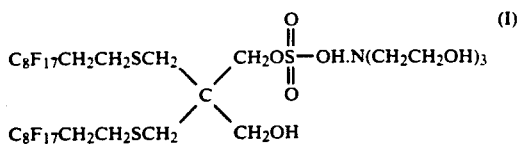

The FAB mass ion observed for structure (I) is at m/z 1139 and represents the (M-H)-ion. The ion at m/z 1219 also observed in the spectrum reveals the presence of minor amount of the di-sulfate (II).

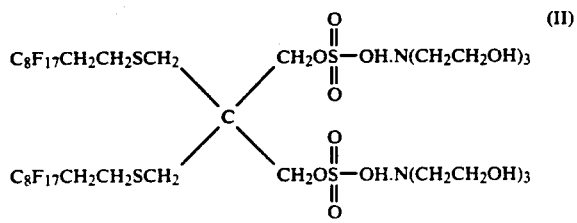

EXAMPLE 2

2,2-Bis(1,1,2,2-tetrahydroperfluorodecylsulfonylmethyl)-1,3-propanediol (15 g, 0.013 mole) is charged into a three-neck flask with diethylene glycol dimethyl ether (17.4 g). Stirring is started under nitrogen flow. The solution is cooled to 0° C. and 95% H₂SO₄ (5.1 g, 0.052 mole) is added dropwise to the solution so the temperature does not exceed 25° C. The addition is complete in ten minutes. The solution is allowed to warm to 25° C. and stirring is continued for 48 hours. Triethanol amine (17.5 g, 0.12 mole) in H₂O (47.6 g) is slowly added to the solution so the temperature does not exceed 45° C. The pH is 7.15 and the solution contains 17.6% actives of the formula

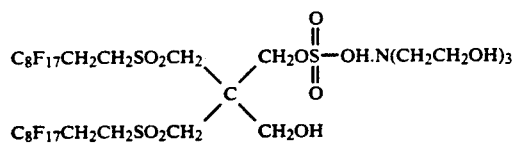

EXAMPLE 3

2,2-Bis(1,1,2,2-tetrahydroperfluoroalkylthiomethyl)-1,3-propanediol* (400 g, 0.38 mole) is charged into a three-neck flask with ethylene glycol dimethyl ether (451 g). Stirring is started under nitrogen flow. The solution is cooled to 0° C. and 95% H₂SO₄ (149 g, 1.52 mole) is added dropwise to the solution so the temperature does not exceed 25° C. The addition is complete in ten minutes. The solution is allowed to warm to 25° C. and stirring is continued for 48 hours. Triethanol amine (553 g, 3.7 mole) in H₂O (1214 g) is slowly added to the solution so the temperature does not exceed 45° C. The pH is 7.45 and the solution contains 17.6% actives of the formula

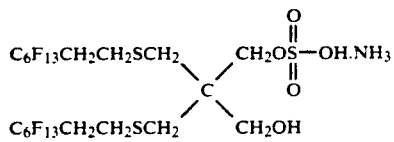

\* wherein perfluoroalkyl is a mixture of $C_6F_{13}$, $C_8F_{17}$, $C_{10}F_{21}$, $C_{12}F_{25}$, $C_{14}F_{29}$ and $C_{16}F_{33}$ and the average chain length is $C_8F_{17}$.

EXAMPLE 4

2,2-Bis(1,1,2,2-tetrahydroperfluorooctylthiomethyl)-1,3-propanediol (36.5 g, 0.043 mole) is charged into a three-neck flask with diethylene glycol dimethyl ether (19.8 g). Stirring is started under nitrogen flow. The solution is cooled to 0° C. and 95% $H_2SO_4$ (16.7 g, 0.17 mole) is added dropwise to the solution so the temperature does not exceed 25° C. The addition is complete in ten minutes. The solution is allowed to warm to 25° C. and stirring is continued for 48 hours.

The solution separates into two layers and the upper layer (solvents) is discarded. The lower layer is neutralized to pH 9.1 using concentrated ammonium hydroxide (15.5 g, 0.26 moles) in water (48 g). The resulting solution is found to contain

Surface tension: dynes/cm in distilled water (% solids): 19.4 (0.1); 28.7 (0.01); 43.8 (0.001).

EXAMPLE 5

2,2,2-Tris(1,1,2,2-tetrahydroperfluorodecylthiomethyl)-1-ethanol (15 g, 0.01 mole) is charged into a three neck round bottom flask with ethylene glycol dimethyl ether (20.76 g). The solution is stirred under nitrogen and cooled to 0° C. Chlorosulfonic acid (1.74 g, 0.025 mole) is added to the solution slowly so the temperature does not exceed 25° C. Once the addition is complete the solution is allowed to warm up to 25° C. and stirring is continued for 35 minutes. The solvent is removed under reduced pressure to yield a tan solid containing $(C_8F_{17}CH_2CH_2SCH_2)_3$—C—$CH_2OSO_3H$.

EXAMPLES 6-15

Using the methods described and by techniques similar to Examples 1-5, the following additional thio-, sulfonyl-, ether, and amino-sulfates are prepared.

| Example | Perfluoroalkyl Terminated Neopentyl Sulfates |
|---|---|
| 6 | $HO_3SOCH_2C(CH_2OCH_2CF_3)_2CH_2OSO_3H$ |
| 7 | $HO_3SOCH_2C(CH_2SO_2CH_2CH_2CH_2CH_2C_6F_{13})_2CH_2OSO_3H$ |
| 8 | $HO_3SOCH_2C(CH_2SO_2CH_2CH_2C_6F_{13})_2CH_2OH$ |
| 9 | $HO_3SOCH_2C(CH_2SCH_2CH_2N(CH_3)CH_2CH_2C_8F_{17}CH_2OH$ |
| 10 | $HO_3SOCH_2C[CH_2N(CH_3)SO_2C_8F_{17})_2CH_2OH$ |
| 11 | $HOCH_2C(CH_2SCH_2CH_2NHSO_2CH_2CH_2C_6F_{13})_2CH_2OSO_3H$ |
| 12 | $HO_3SOCH_2C(CH_2SCH_2CH_2NHCOC_7F_{15})_2CH_2OH$ |
| 13 | $HO_3SOCH_2C[CH_2N(CH_3)CH_2CH_2C_8F_{17})_2CH_2OSO_3H$ |
| 14 | $HO_3SOCH_2C[CH_2OH)_2CH_2SCH_2C_8F_{17}$ |
| 15 | $HO_3SOCH_2C(CH_2OCH_2CH_2C_8F_{17})_3$ |

EXAMPLE 16

This example describes comparative external size performance of the perfluoroalkyl sulfates of the present invention Examples 1-3 against a commercial phosphate size - SCOTHBAN FC-807 (3M Co.), a bis-perfluoroalkyl phosphate ester, ammonium salt. The products are applied to paper by pad application and tested for Oil Kit Rating and the Grease Resistance Test.

The results indicate that the perfluoroalkyl sulfates of the present invention have superior performance at much lower application levels, by the Grease Resistance Test. Further, the novel sulfates pass the Grease Resistance Test at lower Kit Numbers. This allows their application to products requiring better adhesive bonding and better label adhesion. It further permits the manufacturer to have lessened problems with printing.

| | % Fluorine on Wt. of Paper | Oil Kit Number | Grease Resistance Test Test |
|---|---|---|---|
| Example 1 | .035 | 3 | pass |
| | .055 | 8 | pass |
| | .065 | 11 | pass |
| Example 2 | .035 | 3 | pass |
| | .055 | 5 | pass |
| | .065 | 7 | pass |
| Example 3 | .035 | 3 | fail |
| | .055 | 6 | pass |
| | .065 | 10 | pass |
| FC-807 Phosphate | .035 | 3 | fail |
| | .055 | 6 | fail |
| | .065 | 7 | pass |

What is claimed is:

1. A perfluoroalkyl substituted sulfate compound of the formula $$(R_fXCH_2)_xC(CH_2OH)_y(CH_2OSO_3-M+)_z \quad (I)$$

or $$(R_fEXCH_2)_xC(CH_2OH)_y(CH_2OSO_3-M+)_z \quad (II)$$

wherein $R_f$ is a straight or branched chain perfluoroalkyl of 1 to 18 carbon atoms or said perfluoroalkyl substituted by perfluoroalkoxy of 2 to 6 carbon atoms, or mixtures thereof, E is branched or straight chain alkylene of 1 to 10 carbon atoms or said alkylene interrupted by one to three groups selected from the group consisting of —NR—, —O—, —S—, —SO$_2$—, —COO—, —OOC—, —CONR—, —NRCO—, —SO$_2$NR— and NRSO$_2$— or terminated at the $R_f$ end with —CONR— or —SO$_2$NR—, where $R_f$ is attached to the carbon or sulfur atom, and for formula II, X is —S—, —O—, —SO₂—, or —NR—, and for formula I, X is —CONR— or —SO₂NR—, where R$_f$ is attached to the carbon or sulfur atom, and where R is independently hydrogen, alkyl of 1 to 6 carbon atoms or hydroxyalkyl of 2 to 6 carbon atoms; x is 1, 2 or 3; y is 0, 1 or 2; z is 1, 2 or 3; x+y+z=4; M is independently hydrogen, an alkali metal or organoammonium ion.

2. A compound according to claim 1, wherein R$_f$ is perfluoroalkyl of 2 to 14 carbon atoms, or perfluoroalkyl of 2 to 6 carbon atoms substituted by perfluoroalkoxy of 2 to 6 carbon atoms.

3. A compound according to claim 2, wherein E is alkylene of 2 to 6 carbon atoms, —CONHCH₂CH₂—, —CH₂CH₂N(CH₃)CH₂CH₂—.

4. A compound according to claim 3, wherein X is —S— or —SO₂—.

5. A compound according to claim 2, wherein R$_f$ is perfluoroalkyl of 6–14 carbon atoms.

6. A compound according to claim 5 of formula II wherein E is alkylene of 2 to 6 carbon atoms, or said alkylene interrupted by a group selected from the group consisting of —NR—, —O—, —S—, —SO₂—, —O₂C—, —CONR—, and —SO₂NR.

7. A compound according to claim 6, wherein E is ethylene.

8. A compound according to claim 6, wherein X is —S— or —SO₂—.

9. An aqueous solution for rendering cellulosic or natural or synthetic polyamide materials oil and water repellant comprising:
(a) about 0.01 to about 5% by weight of the compound of claim 1,
(b) 0 to about 3% by weight emulsifier;
(c) 0 to about 5% water repellant resistant, filler, bacteriostat, coloring agent, or surface conditioner adjuvant, or mixtures thereof;
(d) 0 to about 10% sizing agent; and
(e) the remainder water.

10. An aqueous solution for the internal or external sizing of paper pulp comprising:
(a) about 0.005 to 0.19% by weight of a compound of claim 1;
(b) 0 to about 0.05% by weight emulsifier;
(c) 0 to about 5% water filler, bacteriostat, coloring agent, or surface conditioner adjuvant, or retention aid, or mixtures thereof;
(d) 0 to about 10% sizing agent; and
(e) the remainder water.

* * * * *